United States Patent
Jarrott et al.

(10) Patent No.: US 6,881,740 B1
(45) Date of Patent: Apr. 19, 2005

(54) PHARMACEUTICAL AGENTS

(75) Inventors: Bevyn Jarrott, Donvale (AU); Phillip Mark Beart, Ivanhoe (AU); William Roy Jackson, Burwood (AU); Alan Duncan Robertson, South Melbourne (AU); Maree Patricia Collis, Prahran (AU); Alexandra Papanikos, Kilda East (AU)

(73) Assignee: Monash University, Victoria (AU)

( * ) Notice: Subject to any disclaimer, the term of this patent is extended or adjusted under 35 U.S.C. 154(b) by 0 days.

(21) Appl. No.: 09/743,379

(22) PCT Filed: Jul. 8, 1999

(86) PCT No.: PCT/AU99/00558

§ 371 (c)(1),
(2), (4) Date: Jun. 4, 2001

(87) PCT Pub. No.: WO00/02865

PCT Pub. Date: Jan. 20, 2000

(30) Foreign Application Priority Data

Jul. 8, 1998 (AU) .......................................... PP4580/98
Jun. 1, 1999 (AU) .......................................... PQ700/99

(51) Int. Cl.$^7$ .................. C07D 239/49; C07D 239/50; A61K 31/506; A61P 3/10; A61P 9/10
(52) U.S. Cl. ...................................... 514/278; 544/323
(58) Field of Search .......................... 544/323; 514/278

(56) References Cited

U.S. PATENT DOCUMENTS 3,274,190 A    9/1966   Gray et al. .............. 260/249.5

FOREIGN PATENT DOCUMENTS

WO        WO 93/10116        5/1993

OTHER PUBLICATIONS

Abstract of T. Tsuji, et al, "Synthesis of 2–substituted –4,6–diamino–s–triazines", *Chemical Abstracts,* 69:77243 1968.

*Primary Examiner*—Venkataraman Balasubramanian
(74) *Attorney, Agent, or Firm*—Scully, Scott, Murphy & Presser

(57) ABSTRACT

This invention relates to compounds to formula (1) wherein B is optionally substituted aryl; $R^1$ and $R_2$ are the same or different and are independently selected from hydrogen or $C_{1-3}$ alkyl; n is 1 or 2, preferably n is 1; m is 0 or 1; $R^3$ is hydrogen or acyl, $R^4$ and $R^5$ are the same or different and are independently selected from amino, alkylamino, dialkylamino, arylamino and $C_2$–$C_4$ cycloalkylamino; X and Y are independently selected from C, H or N provided at least one of X and Y is N; and salts thereof, solvates thereof, pharmaceutically acceptable derivatives thereof, prodrugs thereof, tautomers thereof and/or isomers thereof, and processes for their reparation and methods of treatment, pharmaceutical formulations and uses involving them.

4 Claims, No Drawings

PHARMACEUTICAL AGENTS

The present invention relates to arylalkylheterocyclic compounds, methods for their manufacture, pharmaceutical formulations of such compounds and their use in therapy, particularly in the treatment of conditions related to neurological damage of the peripheral and/or the central nervous system, or other conditions related to NMDA receptors or voltage-sensitive sodium channels.

Damage to the neurones of the central nervous system may result from acute events that lead to ischaemia or other forms of hypoxia, or from neurodegenerative diseases such as Alzheimer's disease, Parkinson's disease. Huntingion's disease or lateral amyotrophic sclerosis. The mechanism of such neuronal injury is complex, however, extensive investigation of such processes has identified the over stimulation of receptors for excitatory amino acids, for example L-glutamate, and subsequent oxidative processes as playing a role in the pathway to neurodegeneration resulting from both acute ischaemic or anoxic events and a wide variety of chronic neurological disorders (Coyle el al, 1993; and Lipton et al., 1994). These two mechanisms are not totally independent, part of the cascade of events that follow over stimulation of receptors for excitatory amino acids has been shown to be an effective increase in the generation of reactive free radicals. Recent evidence also indicates that two cytodestructive events may be involved in excitotoxic/free radical-induced cell death—necrosis and apoptosis (Bonfoco et al., 1995). The latter event, also termed programmed cell death, is considered to occur in normal development and in the aging process.

Glutamate is the major excitatory neurotransmitter present in the brain and spinal cord, and glutamate receptors are divided into two main subtypes, ionotropic and metabotropic. A particular ionotropic glutamate receptor identified as being involved in excitatory amino acid induced neuronal damage in the brain and central nervous system is the N-methyl-D-aspartate (NMDA) receptor complex (Meldrum et al., 1989; and Choi, 1992). This receptor-ionophore complex has a number of modulatory sites associated with it, including the glycine site, the NMDA or glutamate site, the channel, the polyamine site, a pH sensitive region, a redox site, and a zinc-binding site. Compounds that block the activity of the NMDA receptor complex by binding to these various sites and by preventing subsequent entry of $Ca^{2+}$ have been indicated as neuroprotective agents. For example, ifenprodil and eliprodil have been reported as interacting with the polyamine sensitive binding site of the NMDA receptor (Carter et al., 1989 and 1990; Reynolds et al., 1989; Robinson et al., 1990; Beart et al., 1995) and have been reported as having neuroprotective properties in models of neurodegeneration following ischaemia (Gotti et al., 1988). Compounds that block NMDA receptors have also been indicated as being useful for a number of other conditions. Similarly, compounds that modulate voltage-sensitive sodium channels may also inhibit release of excitatory amino acids and may be useful in neuronal protection (Lysko et al., 1995 and Urenjak et al., 1996) or other conditions related to sodium channels.

Neuropathic pain is often due to damage to peripheral sensory and motor nerves which is then experienced as chronic pain that does not respond to opiates. It is now known that peripheral nerve damage leads to increased sodium channel biosynthesis and expression in peripheral nerves (see Rizzo M. A. et al. (1995) Neurobiology of Disease 2: 87–96; Novakovic S. D. et al. (1998) Journal of neuropathic pain (see Tanelian D. L. & Victory R. A. (1995) Pain Forum 4: 75–80). Since this also occurs in diabetic peripheral neuropathy, sodium channel blockers may also be useful in this painful condition, as well as in the management of intractable cough.

The present invention is directed to the provision of new compounds that block excitatory amino acid activity, preferably at the NMDA receptor complex. Some compounds of the present invention also display an affinity for voltage-sensitive sodium channels.

Accordingly in a first aspect, the present invention provides compounds of formula (I)

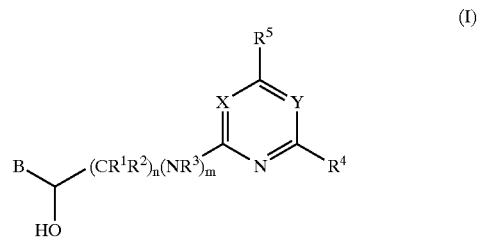

wherein
B is optionally substituted aryl;
$R^1$ and $R^2$ are the same or different and are independently selected from hydrogen or $C_{1-3}$ alkyl;
n is 1 or 2, preferably n is 1;
m is 0 or 1;
$R^3$ is hydrogen or acyl;
$R^4$ and $R^5$ are the same or different and are independently selected from amino, alkylamino, dialkylamino, arylamino and $C_2$–$C_8$ cycloalkylamino;
X and Y are independently selected from C or N provided at least one of X and Y is N; and salts thereof, solvates thereof, pharmaceutically acceptable derivatives thereof, prodrugs thereof, tautomers thereof and/or isomers thereof.

In this specification "aryl" used either alone or in compound words such as "arylamino" or "diarylamino"denotes single, polynuclear, conjugated and fused residues of aromatic hydrocarbons or aromatic heterocyclic ring systems. Examples of aryl include but are not limited to phenyl, naphthyl, fluorenyl, pyrenyl, pyridyl, pyrrolyl, imidazoloyl, pyrazolyl, indolyl, thiophenyl, pyrimidinyl, thiazolyl, quinolinyl, isoquinolinyl, benzofuranyl, benzothienyl, benzodioxanyl, benzodioxolyl and the like.

In this specification "optionally substituted" means that a group may or may not be further substituted by one or more groups selected from alkyl, alkenyl, alkynyl, aryl, fluoro, chloro, bromo, hydroxy, alkyloxy, alkenyloxy, aryloxy, acyloxy, amino, alkylamino, dialkylamino, arylamino, thio, alkylthio, arylthio, cyano, oxo, nitro, acyl, amido, alkylamido, dialkylamido, carboxyl, or two optional substituents may together with the carbon atoms to which they are attached form a 5- or 6-membered aromatic or non-aromatic ring containing 0, 1 or 2 heteroatoms selected from nitrogen, oxygen or sulfur. Optional substituents may themselves bear additional optional substituents. Preferred optional substituents include $C_{1-3}$ alkyl such as for example methyl, ethyl and trifluoromethyl, fluoro, chloro, bromo, hydroxy, $C_{1-3}$ alkyloxy such as for example methoxy, ethoxy and trifluoromethoxy, and amino.

Throughout the specification, the term "alkyl", used either alone or in compound words such as "alkyloxy" is denoted, unless otherwise defined, to mean both the straight chain $C_{1-6}$ alkyl or branched chain $C_{3-6}$ alkyl and the branched or unbranched $C_{3-6}$ cycloalkyl and includes optionally substituted alkyl. Examples of straight chain $C_{1-6}$alkyl and branched chain $C_{3-6}$ alkyl include methyl, ethyl, propyl, isopropyl, butyl, isobutyl, sec-butyl, tert-butyl, hexyl, 4-methylpentyl, 1-methylpentyl, 2-methylpentyl, 3-methylpentyl and the like. Examples of $C_{3-6}$ cycloalkyl include cyclopropyl, cyclobutyl, cyclopentyl, cyclohexyl and the like. Haloalkyl groups such as trifluromethyl are examples of optionally substituted alkyl groups.

Throughout the specification, the term "alkenyl", used either alone or in compound words such as "alkenyloxy" is denoted, unless otherwise defined, to mean both the straight chain $C_{2-6}$ alkenyl or branched chain $C_{3-6}$ alkenyl and the branched or unbranched $C_{3-6}$ cycloalkenyl and includes optionally substituted alkenyl. Examples of straight chain $C_{2-6}$ alkenyl and branched chain $C_{3-6}$ alkenyl include ethylenyl, propenyl, isopropenyl, butenyl, isobutenyl, dimethylbutenyl, pentenyl, methylpentenyl, hexenyl and the like. Examples of $C_{3-6}$ cycloalkyl include cyclobutenyl, cyclopentenyl, cyclohexenyl and the like.

"Acyl" includes a group represented by C(=O)alkyl, C(=O)alkenyl or C(=O)aryl. Acyl groups derived from amino acids are included within the meaning of "acyl".

$C_2$–$C_8$ cycloalkylamino means any cyclic amine containing from 2 to 8 carbons in the ring. The cycloalkylamino ring may contain other atoms and may be optionally substituted. Examples of $C_2$–$C_8$ cycloalkylamino include pyrrolidinyl, piperidinyl, morpholinyl, aziridinyl, pyrrolinyl, pyridinyl and the like.

The following groups are representative examples of the groups B, the preferred point of attachment of the moiety is indicated by an arrow:

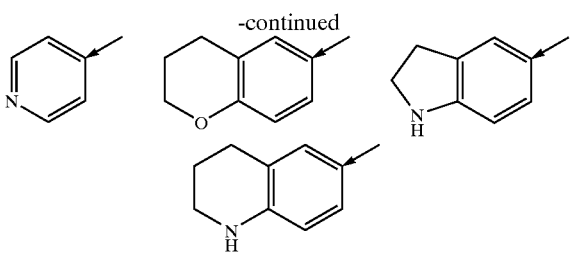

In one preferred group of compounds of formula (1) are those wherein $R^1$ and $R^2$ are hydrogen.

Another preferred group of compounds of formula (1) are those wherein X is CH, Y is N and m is 0.

Yet another preferred group of compounds of formula (1) are those wherein:
B is optionally substituted phenyl
$R^1$ is hydrogen and $R^2$ is selected from hydrogen or $C_{1-3}$ alkyl;
n is 1;
m is 0 or 1;
$R^3$ is hydrogen;
$R^4$ and $R^5$ are the same;
one of X and Y is N and the other is CH.

A further preferred group of compounds of formula (1) are those wherein:
B is optionally substituted phenyl;
$R^1$ and $R^2$ are hydrogen;
n is 1;
m is 0;
$R^4$ and $R^5$ are the same;
X is CH and Y is N.

The salts of the compounds of formula (1) are preferably pharmaceutically acceptable, but it will be appreciated that non-pharmaceutically acceptable salts also fall within the scope of the present invention, since these are useful as intermediates in the preparation of pharmaceutically acceptable salts. The pharmaceutically acceptable salts may include conventional non-toxic salts or quaternary ammonium salts of these compounds, which may be formed, e.g. from organic or inorganic acids or bases. Examples of such acid addition salts include, but are not limited to, those formed with pharmaceutically acceptable acids such as acetic, propionic, citric, lactic, methanesulphonic, toluenesulphonic, benzenesulphonic, salicylic, ascorbic, hydrochloric, orthophosphoric, sulfuric, tartaric and hydrobromic acids. Base salts includes, but is not limited to, those formed with pharmaceutically acceptable cations, such as sodium, potassium, lithium, calcium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

The compounds of the invention may be in crystalline form or as solvates (e.g. hydrates) and it is intended that both forms are within the scope of the present invention. Methods of solvation are generally known within the art.

Pharmaceutically acceptable derivatives may include any pharmaceutically acceptable salt, hydrate or any other compound which, upon administration to a subject, is capable of providing (directly or indirectly) a compound of formula (1) or an therapeutically active metabolite or residue thereof.

Any compound that is a prodrug of a compound of formula (1) is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative.

The compounds of the present invention may exist as an isomer or mixtures of isomers. All such isomeric forms of the compounds of formula (1) are included as part of the present invention. As the compounds of the invention may have one or more chiral centres they are capable of existing in enantiomeric and diastereomeric forms, all such forms whether purified or as mixtures are included within the scope of the terms "isomer" and "isomers" with regard to the present invention. Isomers may be separated or selectively prepared using procedures routinely used by those skilled in the art.

Examples of compounds of general formula (1) which fall within the ambit of the present invention include those listed in TABLE 1 below.

TABLE 1

| Cpd No. | B | $R^1$ | $R^2$ | n | m | $R^3$ | X | Y | $R^4$ | $R^5$ |
|---|---|---|---|---|---|---|---|---|---|---|
| 1 | phenyl | H | H | 1 | 0 | — | CH | N | pyrrolidinyl | pyrrolidinyl |
| 2 |  |  |  |  |  |  | N | CH |  |  |
| 3 |  | H | H | 1 | 1 | H | CH | N |  |  |
| 4 |  |  |  |  |  |  | N | CH |  |  |
| 5 | 4-hydroxyphenyl | H | H | 1 | 0 | — | CH | N | pyrrolidinyl | pyrrolidinyl |
| 6 |  |  |  |  |  |  | N | CH |  |  |
| 7 |  | H | H | 1 | 1 | H | CH | N |  |  |
| 8 |  |  |  |  |  |  | N | CH |  |  |
| 9 | 4-chlorophenyl | H | H | 1 | 0 | — | CH | N | pyrrolidinyl | pyrrolidinyl |
| 10 |  |  |  |  |  |  | N | CH |  |  |
| 11 |  | H | H | 1 | 1 | H | CH | N |  |  |
| 12 |  |  |  |  |  |  | N | CH |  |  |
| 13 | 4-(F$_3$CO)phenyl | H | H | 1 | 0 | — | CH | N | pyrrolidinyl | pyrrolidinyl |
| 14 |  |  |  |  |  |  | N | CH |  |  |
| 15 |  | H | H | 1 | 1 | H | CH | N |  |  |
| 16 |  |  |  |  |  |  | N | CH |  |  |
| 17 | 3-(F$_3$CO)phenyl | H | H | 1 | 0 | — | CH | N | pyrrolidinyl | pyrrolidinyl |
| 18 |  |  |  |  |  |  | N | CH |  |  |
| 19 |  | H | H | 1 | 1 | H | CH | N |  |  |
| 20 |  |  |  |  |  |  | N | CH |  |  |
| 21 | 2-methylphenyl | H | H | 1 | 0 | — | CH | N | pyrrolidinyl | pyrrolidinyl |
| 22 |  |  |  |  |  |  | N | CH |  |  |
| 23 |  | H | H | 1 | 1 | H | CH | N |  |  |

TABLE 1-continued
| Cpd No. | B | R¹ | R² | n | m | R³ | X | Y | R⁴ | R⁵ |
|---|---|---|---|---|---|---|---|---|---|---|
| 24 | | | | | | | N | CH | | |
| 25 | 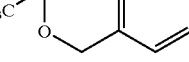 | H | H | 1 | 0 | — | CH | N |  |  |
| 26 | | | | | | | N | CH | | |
| 27 | | H | H | 1 | 1 | H | CH | N | | |
| 28 | | | | | | | N | CH | | |
| 29 | 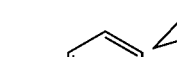 | H | H | 1 | 0 | — | CH | N |  |  |
| 30 | | | | | | | N | CH | | |
| 31 | | H | H | 1 | 1 | H | CH | N | | |
| 32 | | | | | | | N | CH | | |
| 33 | 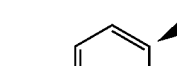 | H | H | 1 | 0 | — | CH | N |  |  |
| 34 | | | | | | | N | CH | | |
| 35 | | H | H | 1 | 1 | H | CH | N | | |
| 36 | | | | | | | N | CH | | |
| 37 | 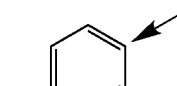 | H | H | 1 | 0 | — | CH | N | NMe₂ | NMe₂ |
| 38 | | | | | | | N | CH | | |
| 39 | | H | H | 1 | 1 | H | CH | N | | |
| 40 | | | | | | | N | CH | | |
| 41 | 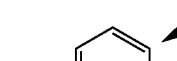 | H | H | 1 | 0 | — | CH | N | NMe₂ | NMe₂ |
| 42 | | | | | | | N | CH | | |
| 43 | | H | H | 1 | 1 | H | CH | N | | |
| 44 | | | | | | | N | CH | | |
| 45 |  | H | H | 1 | 0 | — | CH | N | NMe₂ | NMe₂ |
| 46 | | | | | | | N | CH | | |
| 47 | | H | H | 1 | 1 | H | CH | N | | |
| 48 | | | | | | | N | CH | | |
| 49 |  | H | H | 1 | 0 | — | CH | N | NMe₂ | NMe₂ |
| 50 | | | | | | | N | CH | | |

TABLE 1-continued
| Cpd No. | B | R¹ | R² | n | m | R³ | X | Y | R⁴ | R⁵ |
|---|---|---|---|---|---|---|---|---|---|---|
| 51 | | H | H | 1 | 1 | H | CH | N | | |
| 52 | | | | | | | N | CH | | |
| 53 | 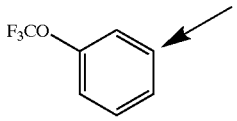 | H | H | 1 | 0 | — | CH | N | NMe₂ | NMe₂ |
| 54 | | | | | | | N | CH | | |
| 55 | | H | H | 1 | 1 | H | CH | N | | |
| 56 | | | | | | | N | CH | | |
| 57 | 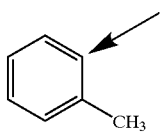 | H | H | 1 | 0 | — | CH | N | NMe₂ | NMe₂ |
| 58 | | | | | | | N | CH | | |
| 59 | | H | H | 1 | 1 | H | CH | N | | |
| 60 | | | | | | | N | CH | | |
| 61 | 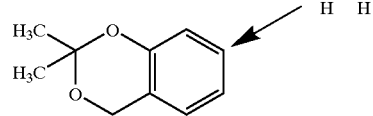 | H | H | 1 | 0 | — | CH | N | NMe₂ | NMe₂ |
| 62 | | | | | | | N | CH | | |
| 63 | | H | H | 1 | 1 | H | CH | N | | |
| 64 | | | | | | | N | CH | | |
| 65 | 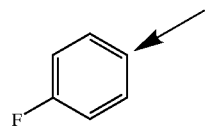 | H | H | 1 | 0 | — | CH | N | NMe₂ | NMe₂ |
| 66 | | | | | | | N | CH | | |
| 67 | | H | H | 1 | 1 | H | CH | N | | |
| 68 | | | | | | | N | CH | | |
| 69 | 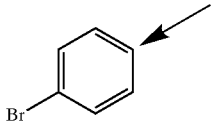 | H | H | 1 | 0 | — | CH | N | NMe₂ | NMe₂ |
| 70 | | | | | | | N | CH | | |
| 71 | | H | H | 1 | 1 | H | CH | N | | |
| 72 | | | | | | | N | CH | | |
| 73 | 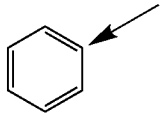 | H | H | 1 | 0 | — | CH | N | NEt₂ | NEt₂ |
| 74 | | | | | | | N | CH | | |
| 75 | | H | H | 1 | 1 | H | CH | N | | |
| 76 | | | | | | | N | CH | | |
| 77 | 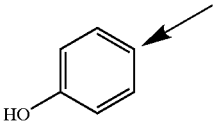 | H | H | 1 | 0 | — | CH | N | NEt₂ | NEt₂ |
| 78 | | | | | | | N | CH | | |

TABLE 1-continued
| Cpd No. | B | R¹ | R² | n | m | R³ | X | Y | R⁴ | R⁵ |
|---|---|---|---|---|---|---|---|---|---|---|
| 79 | | H | H | 1 | 1 | H | CH | N | | |
| 80 | | | | | | | N | CH | | |
| 81 | 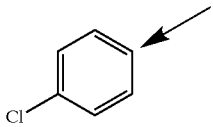 | H | H | 1 | 0 | — | CH | N | NEt₂ | NEt₂ |
| 82 | | | | | | | N | CH | | |
| 83 | | H | H | 1 | 1 | H | CH | N | | |
| 84 | | | | | | | N | CH | | |
| 85 | 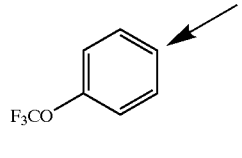 | H | H | 1 | 0 | — | CH | N | NEt₂ | NEt₂ |
| 86 | | | | | | | N | CH | | |
| 87 | | H | H | 1 | 1 | H | CH | N | | |
| 88 | | | | | | | N | CH | | |
| 89 | 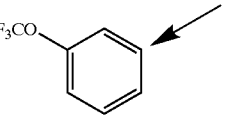 | H | H | 1 | 0 | — | CH | N | NEt₂ | NEt₂ |
| 90 | | | | | | | N | CH | | |
| 91 | | H | H | 1 | 1 | H | CH | N | | |
| 92 | | | | | | | N | CH | | |
| 93 | 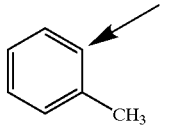 | H | H | 1 | 0 | — | CH | N | NEt₂ | NEt₂ |
| 94 | | | | | | | N | CH | | |
| 95 | | H | H | 1 | 1 | H | CH | N | | |
| 96 | | | | | | | N | CH | | |
| 97 | 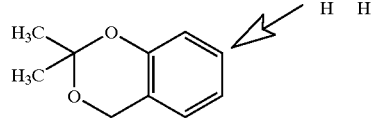 | H | H | 1 | 0 | — | CH | N | NEt₂ | NEt₂ |
| 98 | | | | | | | N | CH | | |
| 99 | | H | H | 1 | 1 | H | CH | N | | |
| 100 | | | | | | | N | CH | | |
| 101 | 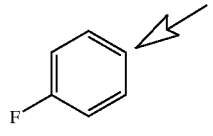 | H | H | 1 | 0 | — | CH | N | NEt₂ | NEt₂ |
| 102 | | | | | | | N | CH | | |
| 103 | | H | H | 1 | 1 | H | CH | N | | |
| 104 | | | | | | | N | CH | | |
| 105 | 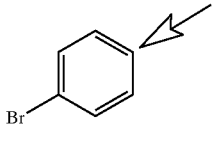 | H | H | 1 | 0 | — | CH | N | NEt₂ | NEt₂ |

TABLE 1-continued

| Cpd No. | B | R¹ | R² | n | m | R³ | X | Y | R⁴ | R⁵ |
|---|---|---|---|---|---|---|---|---|---|---|
| 106 | | | | | | | N | CH | | |
| 107 | | H | H | 1 | 1 | H | CH | N | | |
| 108 | | | | | | | N | CH | | |

Ifenprodil and eliprodil have been reported as antiischaemic agents (Gotti et al., 1988) and both compounds have been reported to associate with the polyamine sensitive site of the NMDA receptor complex (Carter et al., 1989 and 1990; Reynolds et al., 1989; and Robinson et al., 1990). Further reports indicate that compounds that competitively inhibit ifenprodil binding to cortical membranes may also act as antagonists of the polyamine sensitive binding site of the NMDA receptor complex and are potential neuroprotective agents (Beart et al., 1992 and 1995 and WO92/03131). These agents bind independently of the NMDA ion channel (Carter et al., 1991; Reynolds et al., 1989), appear not to cause behavioural effects (Carter et al., 1991), and may target specific heteromeric NMDA receptors (Williams, 1993; Nicola et al., 1994) uniquely distributed in forebrain regions (Standaert et al., 1994) affected in ischaemia and head trauma. It has been found that the compounds of the present invention can inhibit polyamine-sensitive binding of [$^3$H]ifenprodil in rat cerebral cortical membranes according to the procedure of Hashimoto et al., 1994. Accordingly, compounds of the present invention are capable of binding to the NMDA receptor complex and providing a neuroprotective effect, or otherwise providing benefit in other conditions related to NMDA receptors.

The compounds of the invention have also been found to inhibit NMDA induced cell death in cultures of neuronal cells.

Compounds that modulate voltage-sensitive sodium channels may be useful in a number of therapeutic indications including disorders related to neurological damage of the peripheral and/or the central nervous system. Affinity for voltage-sensitive sodium channels may be determined by measuring the displacement of labelled ligands from their binding sites on the sodium channel, for example the procedure of Catterall et al. (1981) uses [$^3$H]-batrachotoxinin A 20-α-benzoate. Compounds of the present invention show an affinity for voltage-sensitive sodium channels in this type of assay.

Some of compounds of the invention have also been found to inhibit voltage-sensitive sodium channels mediated cell death in vitro in cultured cerebellar granule cells.

Accordingly the compounds of the present invention, in view of their NMDA directed and sodium channel activity, are suitable for the control or prevention of disorders related to neurological damage of the peripheral and/or the central nervous system since they may reduce neuronal damage by excitotoxic mechanisms. Those skilled in the art will appreciate that the compounds of the present invention may also be useful in situations where there is a risk of neurological damage of the peripheral and/or the central nervous system.

In view of their voltage-sensitive sodium channel activity the compounds of the present invention may also be useful in the control or prevention of other conditions related to sodium channels.

The in vivo effects of compounds against cerebral ischaemia may be tested in assays such as the Middle Cerebral Artery Occlusion test (Brown et al., 1995).

Accordingly, in a further aspect of the present invention there is provided a method for the prophylactic or therapeutic treatment of one or more disorders related to neurological damage of the peripheral and/or the central nervous system, other conditions related to NMDA receptors, or other conditions related to sodium channels which method includes administering to a subject in need thereof an effective amount of a compound of formula (1) in accordance with the invention.

The present invention also provides the use of a compound of formula (1) in the manufacture of a medicament for use in the treatment of disorders related to neurological damage of the peripheral and/or the central nervous system, other conditions related to NMDA receptors, or other conditions related to sodium channels.

The present invention further provides a compound of formula (1) for use in the treatment of disorders related to neurological damage of the peripheral and/or the central nervous system, other conditions related to NMDA receptors, or other conditions related to sodium channels.

The term "disorders related to neurological damage of the peripheral and/or the central nervous system" is used herein in its broadest sense and includes any disorder or condition that may, result from or cause damage to the neurones of the peripheral and/or the central nervous system.

Examples of disorders of the central nervous system that may be treated in accordance with the present invention include, but are not limited to, acute events that lead to ischaemia or other forms of hypoxia such as head trauma, stroke, cardiac arrest, ischaemia, hypoxia, hypoglycaemia, epilepsy and the like, or neurodegenerative diseases such as Alzheimer's disease, Parkinson's disease or Huntington's disease, lateral amyotrophic sclerosis and variants thereof, and schizophrenia. Examples of disorders of the peripheral nervous system include neuropathic pain, diabetic peripheral neuropathy and other disorders which result in damage to the peripheral sensory and motor nerves.

The term "other conditions related to NMDA receptors" is used herein in its broadest sense and includes any condition or disorder that may benefit from administration of a NMDA receptor modulator.

Examples of other conditions related to NMDA receptors that may be treated in accordance with the present invention include, but are not limited to depression, anxiety, migraine, headaches (including cluster and tension headaches), neurogenic bladder, irritative bladder disturbances, drug dependency (including withdrawal symptoms from alcohol, cocaine, opiates, nicotine and benzodiazepines) and emesis. The relief of pain or anti-nociception may also be achieved using NMDA receptor blockers and are considered also as examples of other conditions related to NMDA receptors.

The term "other conditions related to sodium channels" is used herein in its broadest sense and includes any condition or disorder that may benefit from administration of a voltage-sensitive sodium channel modulator.

Examples of other conditions related to sodium channels that may be treated in accordance with the present invention include, but are not limited to, epilepsy or epileptic psychotic symptoms, hypertension, diabetic peripheral neuropathy and intractable cough. The relief of pain, such as neuropathic pain, or anti-nociception may also be achieved using sodium channel blockers and are considered also as examples of other conditions related to sodium channels.

Inhibition of calcium channels including those modulated by the NMDA receptor may be useful in diseases and conditions other than those noted above. Those skilled in the art will appreciate that the compounds of the present invention may be useful in the treatment of such other diseases or conditions where antagonism of calcium channels, particularly those modulated through the NMDA receptor may be of benefit.

The subject may be a human or an animal such as a domestic or wild animal, particularly an animal of economic importance.

By an "effective amount" is meant a quantity of active compound which will upon single or multiple dose administration to the subject be effective in the control or prevention of a disorder or condition or in achieving a blood or tissue level in the subject that corresponds to a concentration of the active compound that has been shown to provide control or prevention of a disorder or condition in an assay used to predict activity of chemical compounds against a disorder or condition.

As used herein the term "control or prevention" in relation to a disorder or condition refers to slowing, interrupting, arresting or stopping the progression of the a disorder or condition or to reducing the extent of the a disorder or condition below that of an untreated control and does not necessarily indicate a total elimination or cessation of the disorder or condition.

When a compound of the invention is administered to a human subject the daily dosage can normally be determined by the attending physician with the dosage generally varying according to the age, weight, and response of the individual subject, as well as the severity of the subject's symptoms. In general a suitable dose of the compound of the invention will be in the range of 0.1 to 50 mg per kilogram body weight of the recipient per day, preferably in the range of 0.5 to 10 mg per kilogram body weight per day. In some instances, a sufficient therapeutic effect can be obtained at lower doses while in others, larger doses will be required. The desired dose is preferably presented as two, three, four, five, six or more sub-doses administered at appropriate intervals throughout the day. These sub-doses may be administered in unit dosage forms, for example, containing 1 to 500 mg, preferably about 10 to 1000 mg of active ingredient per unit dosage form.

The compounds according to the invention hereinafter for ease of reference referred to as the "active ingredient", may be administered for therapy by any suitable route, including oral, rectal, nasal, topical (including buccal and sublingual); vaginal and parenteral (including subcutaneous, intramuscular, intravenous and intradermal). It will be appreciated that the preferred route will vary with the condition, the age of the subject and the chosen active ingredient. The treatment method of the invention may be used in combination therapy wherein the compounds of the invention are administered in conjunction with one or more other pharmaceutically active agents.

The present invention also extends to a pharmaceutical or veterinary composition which includes the active ingredient in association with a pharmaceutically or veterinarily acceptable carrier, diluent, adjuvant and/or excipient.

The compositions of the present invention may include at least one compound of general formula (1); together with one or more pharmaceutically acceptable carriers, diluents, adjuvants and/or excipients therefor, and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual); vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier, diluent, adjuvant and/or excipient which includes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product. When the composition contains other therapeutic agents, the selection will depend on the condition to be treated. For example, when the composition is to be used in the relief of pain it may be administered along with other analgesic agents. Similarly the administration may be performed in conjunction with other therapies, such as pain therapies.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

Tablets may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an inhaler device or an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

Compositions for rectal administration may be presented as a suppository with a suitable base comprising, for example, cocoa butter.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which preferably are isotonic and which may contain antioxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials; and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as hereinabove described, or an appropriate fraction thereof, of an active ingredient.

The compounds according to the invention may also be presented for use in the form of veterinary compositions, which may be prepared, for example, by methods that are conventional in the art. Examples of such veterinary compositions include those adapted for:

(a) oral administration, external application, for example drenches (e.g., aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension;

(c) topical application, e.g. as a cream, ointment or spray applied to the skin; or (d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartame or saccharin. Suitable disintegrating agents include corn starch, methylcellulose, polyvinylpyrrolidine, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or glutan. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

In another aspect of the present invention there is provided a method for the manufacture of the compounds of formula (1).

The compounds where m is 0 can be formed in accordance with the general sequence of Scheme 1. An alkyl dihalopyrimidine or triazine is reacted with appropriate amines under conditions suitable to displace the halogens, usually involving mild heating. Usually the amines inserted will be the same however if different amino groups are desired then the displacement reactions may be performed sequentially using two different amines. The diamino compound is then treated with an alkyl lithium reagent and the lithiated species reacted with a compound of formula 2. L is a leaving group or a group that the lithiated alkylheterocycle will react with, and Z is a group that may be converted to hydroxyl. If n is 0 then L and Z may together form an aldehyde. Compounds of formula (2) are available commercially, may be prepared following literature procedures or may be prepared by simple modification of literature procedures.

Accordingly in one aspect the invention provides a process for the preparation of a compound of formula (I) where m is 0 including the step of:

reacting a compound of the formula

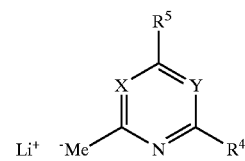

where X, Y, $R^4$ and $R^5$ are as defined above with a compound of formula (2)

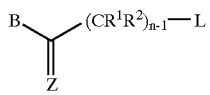

(2)

where $R^1$, $R^2$, B and n are as defined above 1, L is a leaving group and Z is a group capable of being converted to hydroxyl.

To form the compounds where m is 1, the general sequence of Scheme 2 is followed. An amine (3) is reacted with a trihalopyrimidine or triazine under appropriate conditions. The resultant dihalocompound is then reacted with selected amines under conditions suitable to displace the halogens, usually involving mild heating. Usually the amines inserted will be the same however if different amino groups are desired then the displacement reactions may be performed sequentially using two different amines. Compounds of formula (3) are available commercially, may be prepared following literature procedures or may be prepared by simple modification of literature procedures.

Accordingly in another aspect the invention provides a process for the preparation of a compound of formula (I) where m is 1 including the steps of (i) reacting a compound of formula

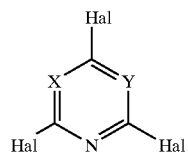

where X and Y are as defined above and Hal is a halogen or halogen-like substituent with a compound of formula (3)

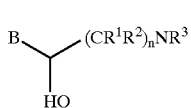

(3)

where B, $R^1$, $R^2$, $R^3$ and n are as defined above; and (ii) reacting product of step (i) with appropriate amine(s) to afford a compound of formula (1) by substitution of Hal.

The products of the reactions hereinbefore described may be isolated by any of the standard procedures known in the art. Such procedures include extraction, recrystallisation and any type of chromatographic separation routinely utilised in organic synthesis, for example column chromatography, flash column chromatography, reverse phase HPLC.

The halogen or halogen-like substituent may be selected from F, Cl, Br, I, triflate, mesylate, diazonium substituents or any other suitable halogen-like substituent of which a person skilled in the art would be aware.

The appropriate amine may be any amine capable of undergoing a substitution reaction with the halogen or halogen-like substituent to provide an $R^4$ and/or $R^5$ substituent on the aromatic ring as defined above in connection with formula (I).

The leaving group may be any suitable leaving group which would be known to a person skilled in the art, and may be selected from the halogen or halogen-like substituents described above.

Protecting groups suitable for the protection of a particular group during a particular reaction may be such as those suggested by Greene, 1991. A protecting group may be removed using conditions known in the art to be suitable for the removal of that particular group.

Scheme 1

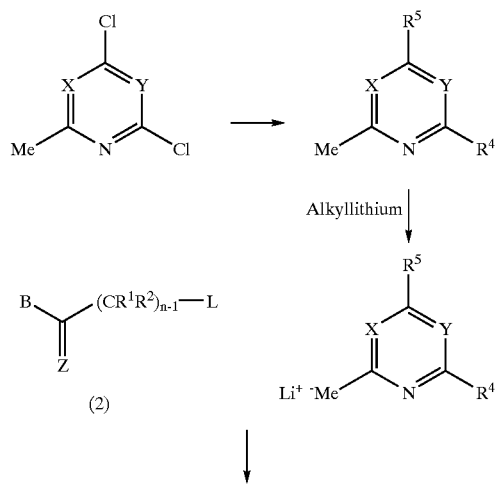

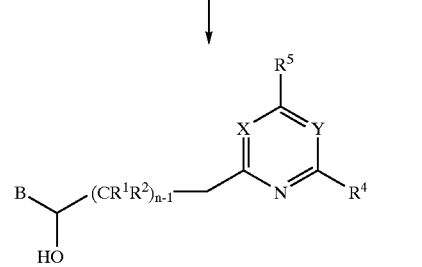

Scheme 2

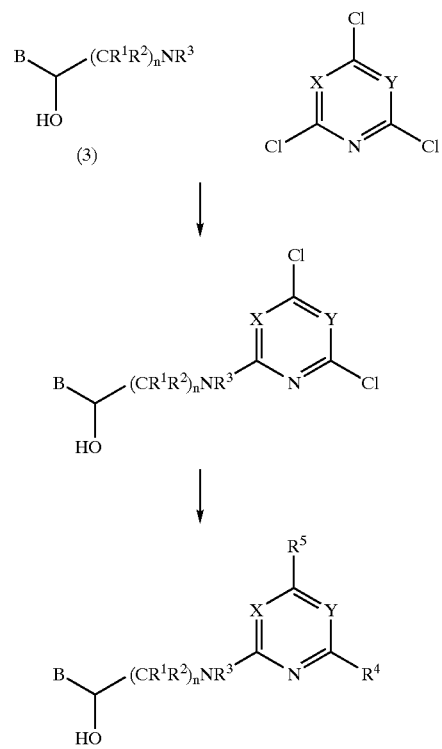

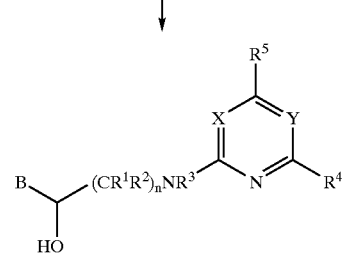

Throughout this specification, unless the context requires otherwise, where the groups B, $R^1$, $R^2$, $R^3$, $R^4$, R, X, and Y appear in Schemes or formulas they have the same meaning as described for formula 1.

EXAMPLES

Examples are provided to assist in the further understanding of the invention. Particular materials, and conditions employed are intended to be illustrative of the invention and not limitative of the reasonable scope thereof.

Example 1

Compound 17

Step A 2,4-Di-N-pyrrolidinyl-6-methyl-pyrimidine 2,4-dichloro-6-methylpyrimidine (1.0 g) was boiled in pyrrolidine at reflux under nitrogen for 4 h. The mixture was cooled and diluted with $CH_2Cl$, then washed with saturated $NaHCO_3$ solution and then saturated NaCl solution. The organic phase was dried over $MgSO_4$ and the solvent removed under reduced pressure to afford a yellow solid. Recrystallisation from ethanol/water gave the desired product as a white solid m.p. 77–78.5° C.

$^1$H.n.m.r. 1.88–1.97, m, 8H; 2.24, s, 3H; 3.23–3.59, m, 8H; 5.51, s, 1H.

Step B 6-[2-hydroxy-2-(3-trifluoromethoxyphenyl) ethyl]-2,4-di-N-pyrrolidinylpyrimidine A solution of n-butyllithium in hexane (1.1 eq) was added to a solution of 2,4-di-N-pyrrolidinyl-6-methylpyrimidine and TMEDA (1.1 eq) in ether under nitrogen. The mixture was boiled at reflux for 1 h then cooled. 3-Trifluoromethoxybenzaldehyde (2 eq) in ether was added and the mixture stirred for two hours at room temperature. The mixture was diluted with water and the aqueous phase extracted twice with ether. The combined organic extracts were dried over $MgSO_4$ and the solvent removed. The residue was purified by flash chromatography (25% Ethyl acetate:hexane) to give the title compound as a pale yellow solid m.p. 100–101° C.

$^1$Hn.m.r. 1.91–1.98, m, 8H; 2.75, d, J 5.8H$_2$, 2H; 3.21–3.58, m, 8H; 5.04, +, J 5.8H$_2$, 1H; 5.44, s, 1H; 7.06–7.10, m, 1H; 7.30–7.36, m, 3H; 7.75, br s, 1H.

The compound was converted to its hydrochloride salt by addition of 1.05 equivalents of hydrogen chloride in ether to a solution of the compound. This was stirred for 1 hour and the hydrochloride salt isolated by filtration.

Examples 2–6

Compound 1, 9, 21, 25, and 29

The compounds were prepared according to the general procedure of example 1 using an appropriate benzaldehyde.

| Compound | m.p. (° C.) (free base) |
| --- | --- |
| 1 | 112–112.5 |
| 9 | 189–192 |
| 21 | 197–197 |
| 25 | 161–161.4 |
| 29 | 148.2–148.6 |

Examples 7 and 8

Compounds 3 and 4

Step A 6-[(2'-hydroxy-2'-phenyl)ethylamino]-4,6-dichloropyrimidine and 2-[(2-hydroxy-2-phenyl) ethylamino]-2,4-dichloropyrimidine 2,4,6-trichloropyrimidine in dioxane was added dropwise to a solution of 2-amino-1-phenylethanol (1.2 equivalents) in dioxane. Sodium bicarbonate (6 equivalents) was added to the solution and it was heated at reflux for 2 hours. The mixture was cooled, diluted with water and the pH adjusted to around 10 with aqueous sodium hydroxide (IM). It was then extracted repeatedly with CH2Cl2, the combined organic extracts were dried over MgSO4 and evaporated to leave a yellow gum. Flash chromatography on silica gel (50% ether:hexane) gave two products, a first eluting band which after evaporation provided 2-[(2'-hydroxy-2'-phenylethylamino]-4,6-dichloropyrimidine (m.p. 113.5–114° C.)., and a second eluting band which after evaporation provided 6-[(2'-hydroxy-2'-phenyl) ethylamino]-2,4-dichloropyrimidine.

Step B

2-[(2'-hydroxy-2'-phenyl)ethylamino]-4,6-dichloropyrimidine was boiled in pyrrolidine at reflux under nitrogen for 4 h. The mixture was cooled and diluted with $CH_2Cl_2$, then washed with saturated $NaHCO_3$ solution and then saturated NaCl solution. The organic phase was dried over $MgSO_4$ and the solvent removed under reduced pressure to afford a brown solid. Recrystallisation from ethyl acetate/hexane gave 2-[(2'-hydroxy-2'-phenyl)ethylamino]-4,6-dipyrrolidin-1-ylpyrimidine (Compound 4) as a white solid.

$^1$H.n.m.r. (CDCl$_3$) 1.95, m, 8H; 3.49, m, 8H; 3.58, m, 2H; 4.68, s 1H; 4.90, d, J=3.6 Hz, 2H; 7.23, t, J=7.2 Hz, 1H; 7.34, m, 2H; 7.41, d, J=7.3 Hz, 2H, 7.71, br s, 1H.

6-[(2'-hydroxy-2'-phenyl)ethylamino]-2,4-dichloropyrimidine was boiled in pyrrolidine at reflux under nitrogen for 4 h. The mixture was cooled and diluted with $CH_2Cl_2$, then washed with saturated $NaHCO_3$ solution and then saturated NaCl solution. The organic phase was dried over $MgSO_4$ and the solvent removed under reduced pressure to afford a brown solid. Recrystallisation from ethyl acetate/hexane gave 6-[(2'-hydroxy-2'-phenyl)ethylamino]-2,4-dipyrrolidin-1-ylpyrimidine (Compound 3) as a white solid.

$^1$H.n.m.r. (CDCl$_3$) 1.85, m, 8H; 3.22, m, 8H; 3.44, m, 2H; 4.73, m, 1H; 4.80, s, 1H; 6.1 br s, 1H; 6.2, br s, 1H; 7.23, m, 1H; 7.34, m, 4H.

The compound were converted to their hydrochloride salts by addition of 1.05 equivalents of hydrogen chloride in ether to a solution of the compound in ether or THF. The mixture was stirred for 1 hour and the hydrochloride salt isolated by filtration.

Examples 9–11

Compounds 11, 15, and 16

The compounds were prepared according to the general procedure of examples 7 and 8 using an appropriately substituted 2-amino-1-phenylethanol. Appropriately substituted 2-amino-1-phenylethanols are available commercially, may be prepared following literature procedures, or may be prepared by simple modification of literature procedures.

| Compound | data (free base) |
| --- | --- |
| 11 | m.p. 183–185° C. |
| 15 | Mass Spec (ESI, CH3CN) M/z 438.1 [M + H]$^+$ |
| 16 | $^1$H.n.m.r. (CDCl$_3$) 1.93–1.98, m, 8H; 3.42–3.66, m, 10H; 4.68, s 1H; 4.90, d, J=3.6Hz, 2H; 7.17, d, |

| Compound | data (free base) |
|---|---|
| | J=7.4Hz, 2H; 7.43, d, J=7.4Hz, 2H. |

Biological Activity

For convenience the results tabulated below refer to the compounds as the free base, however compounds may have been tested either as the free base or as a salt, typically salts used were the hydrochloride.

NMDA Assay Procedure

Tissue Preparation

Briefly, crude membrane suspensions containing 10% rat cerebral cortex were prepared in aqueous 50 mM Tris-HCl buffer (pH 7.4, 4° C.), using a Polytron homogeniser.

NMDA/Polyamine Sites

Assays contained 100 µl of cortex homogenate, [$^3$H]-ifenprodil (4 nM) and various concentrations of test drug. Nonspecific binding was determined using spermine (10 µM).

The sigma receptor ligand 3PPP(+)-3-(3-hydroxyphenyl)-N-propyl-piperidine (100 µM) was included in all tubes to block binding to sigma receptors. Incubation was for two hours at 4° C., ie., conditions favourable to NMDA/polyamine receptor binding. Assays were terminated with ice-cold buffer by rapid vacuum filtration using a Brandel Cell Harvester, through GF/B filter paper, presoaked in 0.025% polyethylimine. Filterpapers were collected, combined with scintillant and bound radioactivity determined using a Packard Scintillation counter.

Sigma Sites

Assays were carried out as for NMDA/polyamine sites with the following exceptions.

Nonspecific binding was defined using 1,3-di-o-tolylguanidine (DTD, 50 µM). Spermine (10 mM) was included in all tubes to block binding to NMDA/polyamine receptors. Incubation conditions were for 1 hr at 37° C., before termination as above.

Data Analysis

Competition curves obtained for drugs active in each assay were analysed using the computer binding analysis program Radlig, using $K_d$=5.72 nM and 2.78 nM for polyamine/NMDA assays respectively. The Ki of some of the compounds of the present invention is shown in Table 2.

TABLE 2

| Compound | IC$_{50}$ (µM) | K$_i$ (µM) |
|---|---|---|
| 9 | 0.400 ± 0.057 | 0.156 ± 0.018 |
| 17 | 4.33 ± 1.56 | 1.40 ± 0.047 |
| 21 | 4.05 ± 0.236 | 1.32 ± 0.241 |

Assay for NMDA-induced Toxicity in Neuronal Cultures

Neuronal cell death was assessed using a 3-(4,5-dimethylthiazol-2-yl)-2,5-diphenyltetrazoliurn bromide (MTT) assay in which NMDA-induced cellular changes are reflected as altered mitochondrial activity (Ankarcrona et al., 1995), as estimated by the formation of a formazan dye, which is measured spectrophotometrically. The procedure employed is essentially that of Roehlm et al. (1991) with minor modifications as previously described elsewhere in work from our laboratories Larm et al. (1996).

Primary cultures of murine neocortical neurones were established as described elsewhere (Larm et al., 1996). The effects of experimental compounds were tested in the cultures at 8 days in vitro. Exposure to NMDA (600 µM, 1 h) and other compounds was performed in an humidified incubator (5% $CO_2$, 8% $O_2$) at 37° C. in anti-oxidant free medium with compounds under evaluation being added 30 min prior to NMDA. For these conditions the culture medium was modified by omitting the following components: D,L- -tocopherol, D,L- -tocopherol acetate, catalase, superoxide dismutase and L-glutamine. Other details are described in Larm et al. (1996). Absorbence was read at 570 nm using a Ceres UV900 microplate reader. Control cultures were included in each experiment containing either vehicle alone or vehicle plus compound. These controls were taken as 100% neuronal viability, under the experimental conditions, and each experiment also included 500 µM L-glutamate representing 100% glutamatergic neuronal cell death. Background cell death in vehicle control cultures was 5–8%. Concentration-response curves were generated as described elsewhere (Larm et al., 1996). The EC$_{50}$ for inhibition of NMDA-induced toxicity by some compounds of the present invention is shown in Table 3.

TABLE 3

| Compound | EC$_{50}$ (µM) |
|---|---|
| 17 | 1.7 |

Sodium Channel Binding Assay

The general procedure of Catterall et al. (1981) was used with minor modifications. Generally, washed rat brain homogenates (350 µL of a 25 mg/mL membrane preparation) were incubated with [$^3$H]-batrachotoxinin A 20-a-benzoate (final assay concentration up to 1.5 nM) and scorpion toxin (from Leiurus quinquestriatus [Sigma Catalogue No. V5251]) (final assay concentration up to 40 g/mL) with and without the test compound over a concentration range of $10^{-8}$ to $10^{-4}$ M in HEPES buffer (50 mM HEPES dissolved in 50 mM Tris HCl pH 7.4 and containing 130 mM choline chloride, 5.4 mM KCl, 0.8 mM MgSO4, 5.5 mM glucose) in a final volume of 500 µL. Non-specific binding was defined using a saturating concentration of veratridine (0.1 mM) and a range of concentrations of [$^3$H]-batrachotoxinin A 20-α-benzoate. The assay tubes are incubated for 30 minutes at 37° C. before termination by rapid filtration through GF/B filter paper and washing using a cell harvester. Bound radioactivity is assessed using a scintillation counter. From dose response curves approximate IC$_{50}$ values for the test compounds were determined. IC$_{50}$ values for some of the compounds of the present invention are shown in Table 4.

TABLE 4

| Compound | IC$_{50}$ µM |
|---|---|
| 9 | 0.77 |
| 17 | 0.42 |

Veratridine Induced Toxicity in Neuronal Cultures

Veratridine is a steroidal plant alkaloid which affects activation of voltage-dependent Na$^+$ channels. The ability of some of the compounds of the present invention to prevent Na$^+$ channel mediated cell death in vitro has been assessed in cultured cerebellar granule cells (Calloway et al. and Cheung et al) Briefly, cerebellar granule cells taken from 7 day old mice were grown in culture for 7–8 days. The cells were pre-incubated with drug for 30 minutes prior to a 60 minute exposure to veratridine (100 µM). Drug remained in the medium during exposure to veratridine. Cell viability was assessed at 18 hours by MTT assay. $EC_{50}$ values were determined using a curve fitting program (Prism GraphPad) and the maximum protection achieved by the compounds are presented in Table 5 below.

TABLE 5

| Compound | $EC_{50}$, μM |
|---|---|
| 9 | 4.0 |
| 17 | 1.7 |

Throughout this specification, unless the context requires otherwise, the word "comprise", or variations such as "comprises" or "comprising" will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said steps or features.

REFERENCES

Ankarcrona M. et al., Neuron, 15, 961–973 (1995)
Beart, P. M. et al., Br. J. Pharmacol., 114, 1359–1364 (1995)
Beart, P. M. et al., Mol. Neuropharmacol., 2, 113–119 (1992)
Bonfoco, E. et al., Proc. Natl. Acad. Sci. USA., 92, 7162–7166 (1995)
Brown, C. M., et al., Br. J. Pharmacol., 115, 1425–1432 (1995)
Callaway J. K., et al., Proc. Australian Neurosci. Soc., 10, 222 (1999)
Carter, C. J. et al., Eur. J. Pharmacol., 164, 611–612 (1989)
Carter, C. J. et al., J. Pharmacol. Exp. Ther., 253, 475482 (1990)
Catterall, W. A., et al., J. Biol. Chem., 256, 8922–8927 (1981)
Cheung N. S. et al., J. Neurosci. Res., 52, 69–82 (1998)
Choi, D. W. et al., J Neurobiol., 23, 1261–1276 (1992)
Gotti, B. et al., J. Pharmacol. Exp. Ther., 247, 1211–1221 (1988)
Greene, T. W. (I 991) Protective Groups in Organic Synthesis, John Wiley and Sons, Inc.
Hashimoto, K., et al., Eur. J. Pharmacol. Mol. Pharmacol., 266, 67–77 (1994)
Larm, J. A. et al., Eur. J. Pharmacol., 314, 249–254 (1996)
Lipton, S. A. et al., N. Engl. J. Med., 330, 613–622 (1994)
Lysko, P. G. et al., Stroke, 25, 2476–82 (1995)
Meldrum, B. et al, Trends Pharmacol. Sci., 11, 379–387 (1990)
Mercer, L. D. et al., J Neurochem, 61, 120–126 (1993)
Nicola, C. et al., J: Neurochem, 63, 2248–2258 (1994)
Reynolds, 1. J. et al., Mol. Pharmacol., 36, 758–765 (1989)
Robinson, T. N. et al., Mol. Neuropharmacol., 1, 31–35 (1990)
Roehm, N. W. et al., Immuno. Methods, 142, 257- (1991)
Standaert, D. G. et al., Comp. Neurol., 343, 1–6 (1994)
Urenjak, J. et al., Pharmacol. Rev., 48 28–68 (1996)
Williams, K., Mol. Pharmacol, 44, 851–859(1993)

What is claimed is:

1. A compound of formula (1) selected from:

6-[2-hydroxy-2-(4-chlorophenyl)ethyl]-2,4-di-N-pyrolidinylpyrimidine,

6-[2-hydroxy-2-(3-triflurormethoxyphenyl)ethyl]-2,4-di-N-pyrolidinylpyrimidine and 6-[2-hydroxy-2-(2-methylphenyl)ethyl]-2,4-di-N-pyrolidinylpyrmidine, or pharmaceutically acceptable salts thereof, solvate thereof, or prodrugs thereof.

2. A method for the therapeutic treatment of ischmeic disease comprising administering to a subject in need thereof a therapeutically effective amount of a compound according to claim 1.

3. A method for the therapeutic treatment of diseases selected from the group consisting of head trauma, stroke, cardiac arrest, ischemia, hypoxia, hypoglycemia and epilepsy comprising administering to a subject in need thereof a therapeutically effective amount of a compound according to claim 1.

4. A pharmaceutical composition comprising a pharmaceutically effective amount of a compound according to claim 1 and a pharmaceutical acceptable carrier, diluent, adjuvant, or excipient thereof.

* * * * *